(12) United States Patent
Vickaryous

(10) Patent No.: US 10,709,485 B2
(45) Date of Patent: Jul. 14, 2020

(54) NEUTRALIZATION PLATE AND RELATED METHODS

(71) Applicant: Brian K. P. Vickaryous, Longwood, FL (US)

(72) Inventor: Brian K. P. Vickaryous, Longwood, FL (US)

( * ) Notice: Subject to any disclaimer, the term of this patent is extended or adjusted under 35 U.S.C. 154(b) by 36 days.

(21) Appl. No.: 16/025,397

(22) Filed: Jul. 2, 2018

(65) Prior Publication Data

US 2019/0000516 A1    Jan. 3, 2019

Related U.S. Application Data

(60) Provisional application No. 62/527,200, filed on Jun. 30, 2017.

(51) Int. Cl.
| | |
|---|---|
| *A61B 17/88* | (2006.01) |
| *A61B 17/80* | (2006.01) |
| *A61B 17/06* | (2006.01) |
| *A61B 17/56* | (2006.01) |
| *A61B 17/82* | (2006.01) |
| *A61B 17/04* | (2006.01) |

(52) U.S. Cl.
CPC .... *A61B 17/8061* (2013.01); *A61B 17/06166* (2013.01); *A61B 17/8057* (2013.01); *A61B 17/82* (2013.01); *A61B 2017/044* (2013.01); *A61B 2017/0414* (2013.01); *A61B 2017/564* (2013.01)

(58) Field of Classification Search
USPC ............... 606/280–299, 902–906, 70–71
See application file for complete search history.

(56) References Cited

U.S. PATENT DOCUMENTS

| | | | |
|---|---|---|---|
| 6,066,141 A | * | 5/2000 | Dall ............... A61B 17/82 606/281 |
| 6,093,201 A | | 7/2000 | Cooper et al. |
| 7,037,308 B2 | | 5/2006 | Medoff |
| 8,551,143 B2 | | 10/2013 | Norris et al. |
| 2010/0179600 A1 | | 7/2010 | Steger et al. |
| 2011/0208198 A1 | | 8/2011 | Anderson et al. |
| 2013/0066378 A1 | | 3/2013 | Gelfand |
| 2013/0090694 A1 | | 4/2013 | Norris et al. |

* cited by examiner

*Primary Examiner* — Sameh R Boles
(74) *Attorney, Agent, or Firm* — Matthew G. McKinney, Esq.; Allen, Dyer et al.

(57) ABSTRACT

A neutralization plate includes a main body, a pair of upper arms extending upwards from the main body, and a pair of lower arms extending downward from the main body to form a generally X-shape with the pair of upper arms. In addition, the neutralization plate includes a horizontal channel formed across a rear side of a midsection of the main body, an aperture formed in the main body between the pair of lower arms and contiguous to a bottom edge of the horizontal channel, and a lower chute formed between the aperture and a lower edge of the horizontal channel. The lower chute is configured for ends of a suture looped through a fractured bone to be passed through the aperture and down the lower chute to a front side of the main body to be anchored separately from the fractured bone.

11 Claims, 8 Drawing Sheets

NEUTRALIZATION PLATE AND RELATED METHODS

RELATED APPLICATION

The present invention is related to U.S. Provisional Patent Application Ser. No. 62/527,200 filed Jun. 30, 2017, the entire contents of which are incorporated herein by reference.

TECHNICAL FIELD

The present invention relates to the field of fracture plating, and, more particularly, to a neutralization plate and related methods.

BACKGROUND

Fractures around the knee and elbow can be difficult to treat due to the limited soft tissue coverage and small size of bone fragments. For example, fractures of the olecranon and patella involve articular surfaces that are treated through anatomic alignment of the joint surface.

These periarticular fractures are traditionally fixed with screw and tension band wiring constructs. The constructs attempt to create a compressive force across the fracture site. For example, in the case of a patella fracture the fragments are loaded in distraction during joint flexion from the pull of the quadriceps and patellar tendons. Accordingly, when affixed with a tension band technique the deep articular surface is loaded in longitudinal compression by the reactive forces across the articular surface and the superficial bone surface is loaded in tension by the pull of a strong muscular insertion such as the quadriceps tendon. As a result, the patella will have a compressive side and a tension side.

A known method of fixation of periarticular fractures includes a technique typically referred to as FIG. 8 tension band wiring. This technique involves driving two stiff stainless steel pins (or screws) longitudinally into bone across the fracture site. A flexible wire is then passed through a drill hole on one side of the fracture site and the two ends of the wire are crossed over the fracture site to the opposite side. One wire is then passed under the ends of the two pins, and the wire twisted and tightened at the other end to develop tension in the wire to produce compression across the fracture site.

The tension band technique holds the tension side of the bone in apposition. This technique results in production of compressive force across the fracture site, resulting in secure fixation, and intended to promote early union of the fracture and early motion of the joint.

At least one shortcoming of the FIG. 8 tension band wiring occurs because standard large pins are used which protrude from the end of the bone at the location where a major tendon inserts. Accordingly, the ends of the pins cause irritation of the soft tissues and require removal. In addition, the tension band wiring can also be uncomfortable as slack in the wire is evident when the joint is extended. The fixation can also be tenuous as advocating early motion can be deleterious to the outcome as the hardware may fail.

Although some improvements to the treatment of periarticular fractures have been developed, there is a need for an improved fixation and neutralization plate.

SUMMARY

In view of the foregoing background, it is therefore an object of the present invention to provide the introduction of the neutralization plate. The neutralization plate includes a main body, a pair of upper arms extending upwards from the main body, and a pair of lower arms extending downward from the main body to form a generally X-shape with the pair of upper arms. In addition, the neutralization plate includes a horizontal channel formed across a rear side of a midsection of the main body, an aperture formed in the main body between the pair of lower arms and contiguous to a bottom edge of the horizontal channel, and a lower chute formed between the aperture and a lower edge of the horizontal channel. The lower chute is configured for ends of a suture looped through a fractured bone to be passed through the aperture and down the lower chute to a front side of the main body to be anchored separately from the fractured bone.

The pair of upper arms include an upper hole and an upper secondary hole in each upper arm, and the pair of lower arms include a lower hole in each lower arm. The main body may also include a lower secondary hole spaced inward from each lower hole on the main body.

An upper chute may be formed on the rear side of the main body between the aperture and the horizontal channel, where the upper chute and the lower chute are sloped and aligned to each other to increase a transfer of compression forces across a fracture via the suture during joint flexion and to neutralize tension forces.

In addition, the neutralization plate may include an upper lip formed on an upper side of the horizontal channel and a lower lip formed on each side of the upper chute. The upper lip and the lower lip each comprises an edge thick enough to prevent the suture from slipping up and over a respective lip. A shape of the neutralization plate is asymmetrical about its horizontal axis.

In another aspect, a method for fixation of a bone fracture using a neutralization plate is disclosed. The method includes feeding a first end of a suture through a bore hole drilled in a fractured bone, positioning the neutralization plate over the fractured bone so that upper arms of the neutralization plate extend above a fracture and the lower arms and aperture of the neutralization plate are below the fracture. The method also includes feeding the suture through a channel of the neutralization plate and the aperture to a front side of the neutralization plate via the lower chute. In addition, the method includes securing the neutralization plate to the fractured bone with plating screws, and tightening the suture isometrically and anchoring ends of the suture to a second bone separately from the fractured bone.

DETAILED DESCRIPTION

Figure 1:
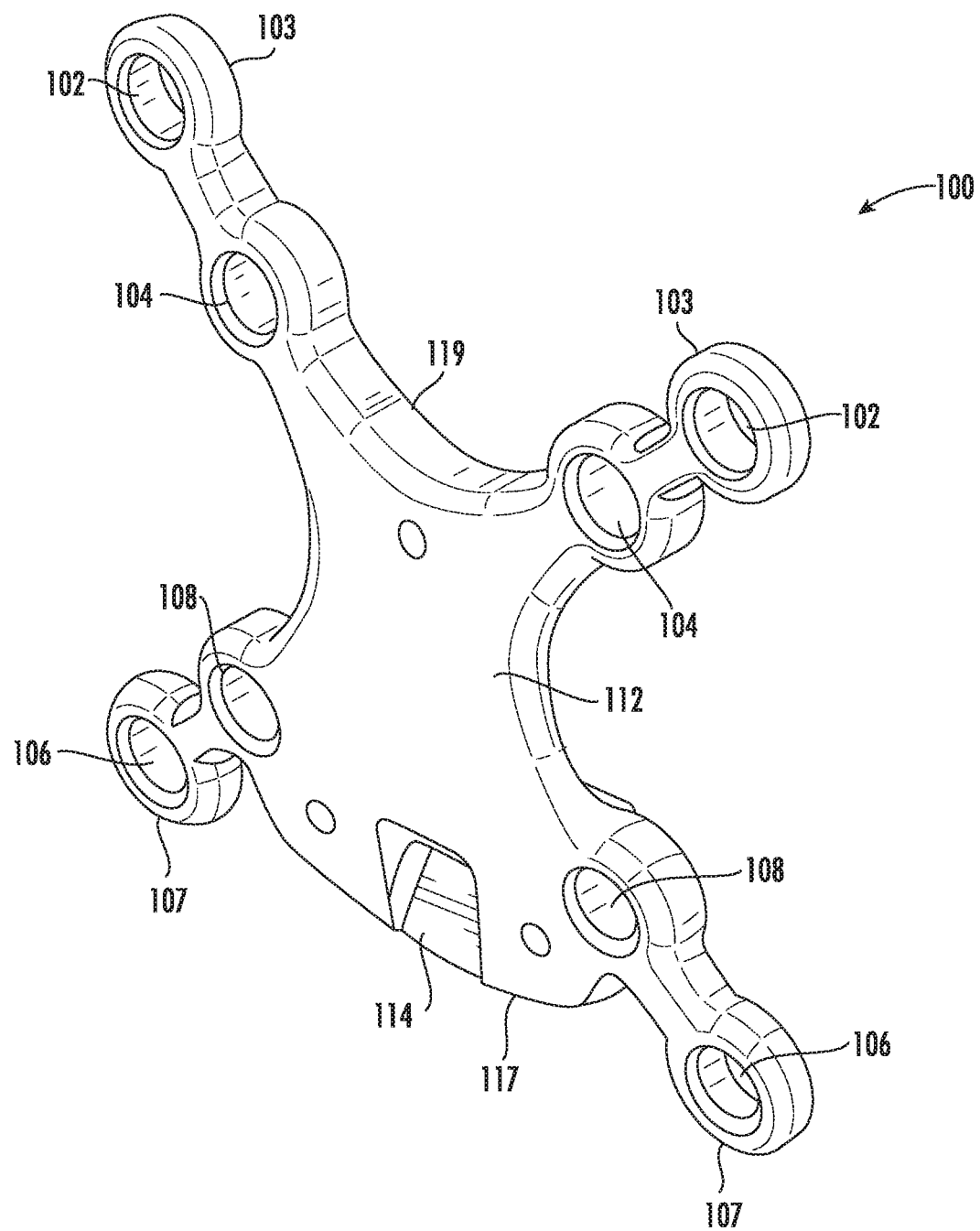
FIG. 1 is a perspective view of a neutralization plate in accordance with a particular embodiment of the invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

In general, in a first aspect, the invention relates to a neutralization plate 100 that functions as a reduction maintaining tool with elements that incorporate a tension neutralization feature when combined with suturing and/or wire to augment and extend fixation. The neutralization plate 100 is intended to be used for the surgical repair of periarticular tensile fractures around the patella, olecranon, greater trochanter, greater tuberosity, radial styloid, lateral and medial malleoli, or lateral malleolus, for example, which occur with relative frequency.

As shown in FIGS. 1 through 8, the neutralization plate 100 may generally be X-shaped. The neutralization plate 100 may be made of any suitable material. For example, the neutralization plate 100 may comprise surgical stainless steel, titanium, polymers, plastics, or any combination thereof.

The neutralization plate 100 includes a main body 112 with upper arms 103 extending away from an upper portion of the main body 112 and lower arms 107 extending away from a lower portion of the main body 112. A plurality of holes are formed in each of its four arms 103, 107 for screw fixation into which screws may be placed to secure the neutralization plate 100 to the fractured bone. The holes may use locking or non-locking screws and may be threaded.

In a particular aspect, upper holes 102 are proximate respective free ends of upper arms 103, and upper secondary holes 104 are located inward on the respective upper arms 103 from the upper holes 102. Similarly, lower holes 106 are proximate the respective free ends of the lower arms 107, and lower secondary holes 108 are located inward from the lower holes 106.

The front surface of the main body 112 of the neutralization plate 100 may have a profile that is relatively smooth without protrusions and may have a similar shape as a surface of the fractured bone to which it is secured.

The neutralization plate 100 includes an upper chute 115 on the rear side of the neutralization plate 100 and a lower chute 114 formed proximate a bottom edge 117. The upper chute 115 is configured to guide a suture and/or wire 130 from the opposing rear side of the neutralization plate 100 through an aperture 110 to the lower chute 114. The suture 130 exits the front side of the neutralization plate 100 as explained in more detail below with respect to FIG. 5, to be tensioned and anchored. The upper chute 115 and the lower chute 114 are sloped and aligned to increase the transfer of compression forces across the fracture via the suture 130 during joint flexion and neutralize tension forces.

Figure 2:
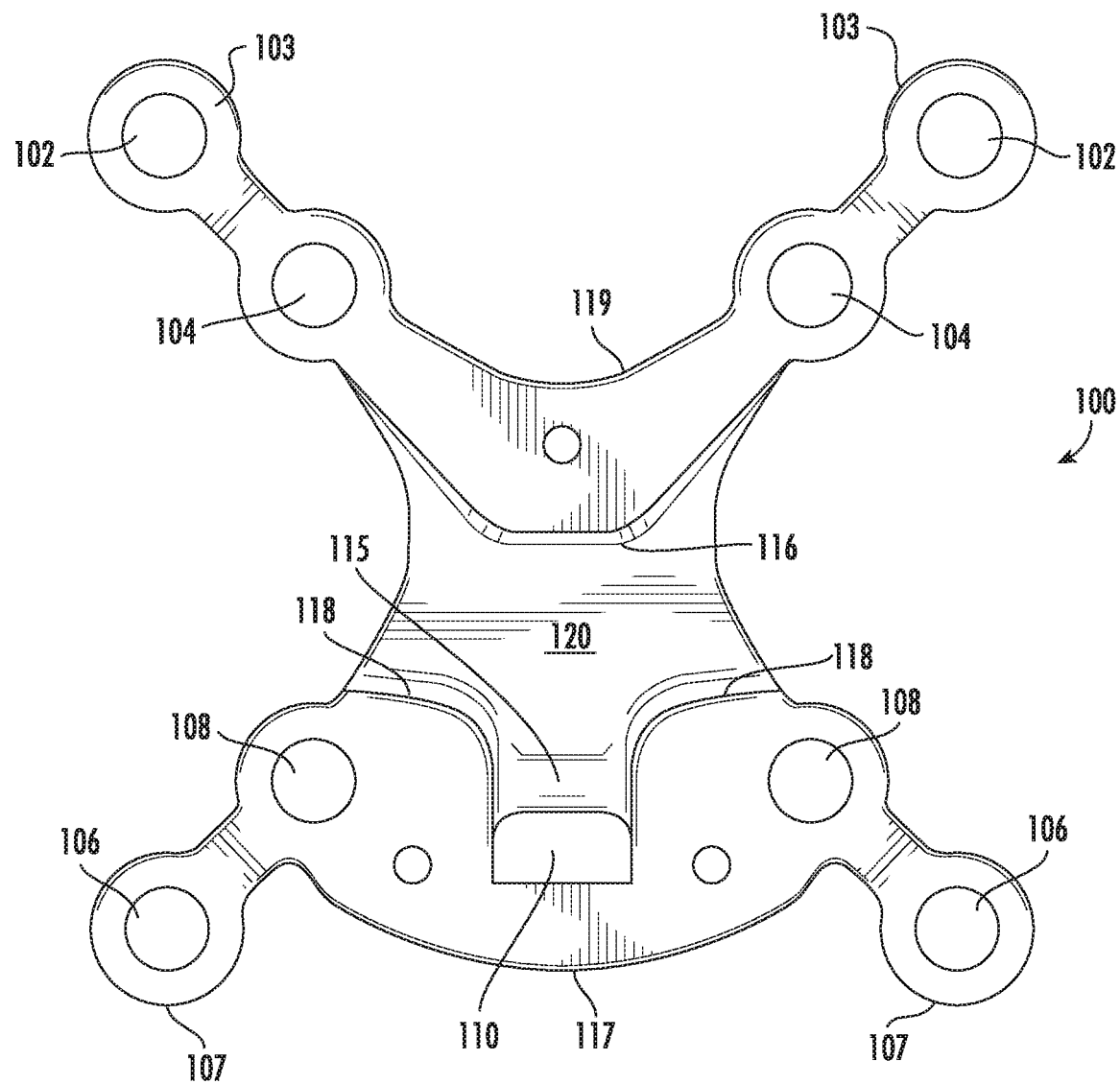
FIG. 2 is a rear view of the neutralization plate.

Referring now to FIG. 2, the rear side of the neutralization plate 100 includes a horizontal channel 120 about its midsection across the main body 112 and spans the rear side of the neutralization plate 100 between the upper arms 103 and the lower arms 107. The channel 120 is formed between an upper lip 116 of the upper arms 103 and a lower lip 118 of the lower arms 107 on the rear side of the neutralization plate 100. The upper lip 116 has an edge thick enough to prevent the suture 130 from slipping up and over the upper lip 106. Similarly, the lower lip 118 is on each side of the upper chute 115 discussed above, and serves to provide a smooth transition for the suture 130 through the aperture 110 defined immediately above the upper chute 115.

Figure 3:
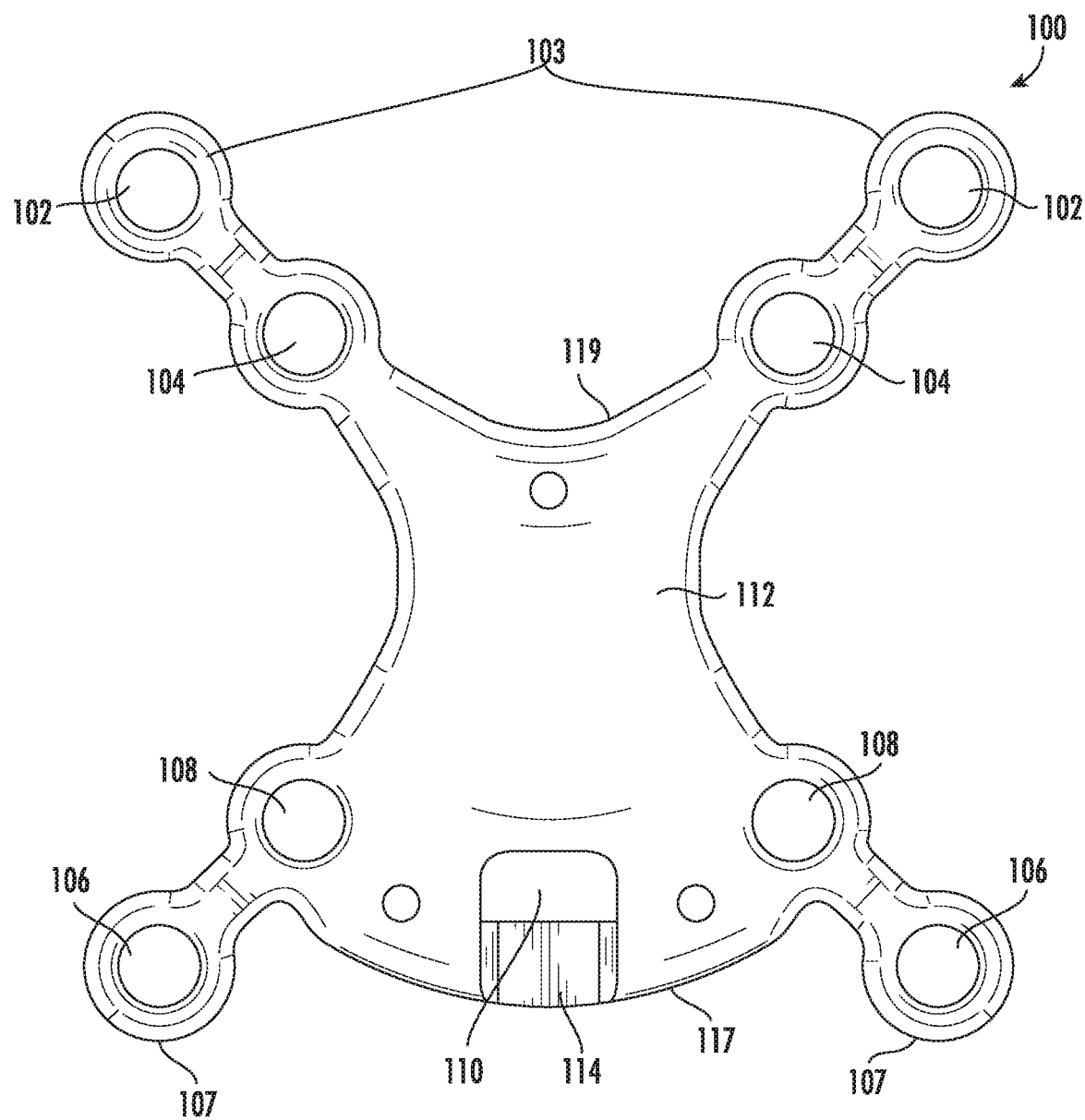
FIG. 3 is a front view of the neutralization plate.

The aperture 110 and the lower chute 114 are aligned as shown in FIG. 3 proximate a bottom edge 117 of the neutralization plate 100. The relative spacing of the holes 102, 104, 106, 108 of the neutralization plate 100 are also more readily apparent in FIG. 3. As can also be seen in FIG. 3, the lower secondary holes 108 are formed within the main body 112 of the neutralization plate 100 rather than in the lower arms 107 themselves in contrast to the upper secondary holes 104.

The neutralization plate 100 is asymmetrical about its horizontal axis where a lower portion of the main body 112 is asymmetrical to the upper portion and the upper chute 115 and the lower chute 114 are formed in the lower portion. In addition, the bottom edge 117 comprises a convex shape to support the lower and upper chutes 114, 115 therein. The upper edge 119 of the main body 112 comprises a concave shape to reduce unneeded material of the neutralization plate 100 and to increase comfort to the patient.

Figure 4:
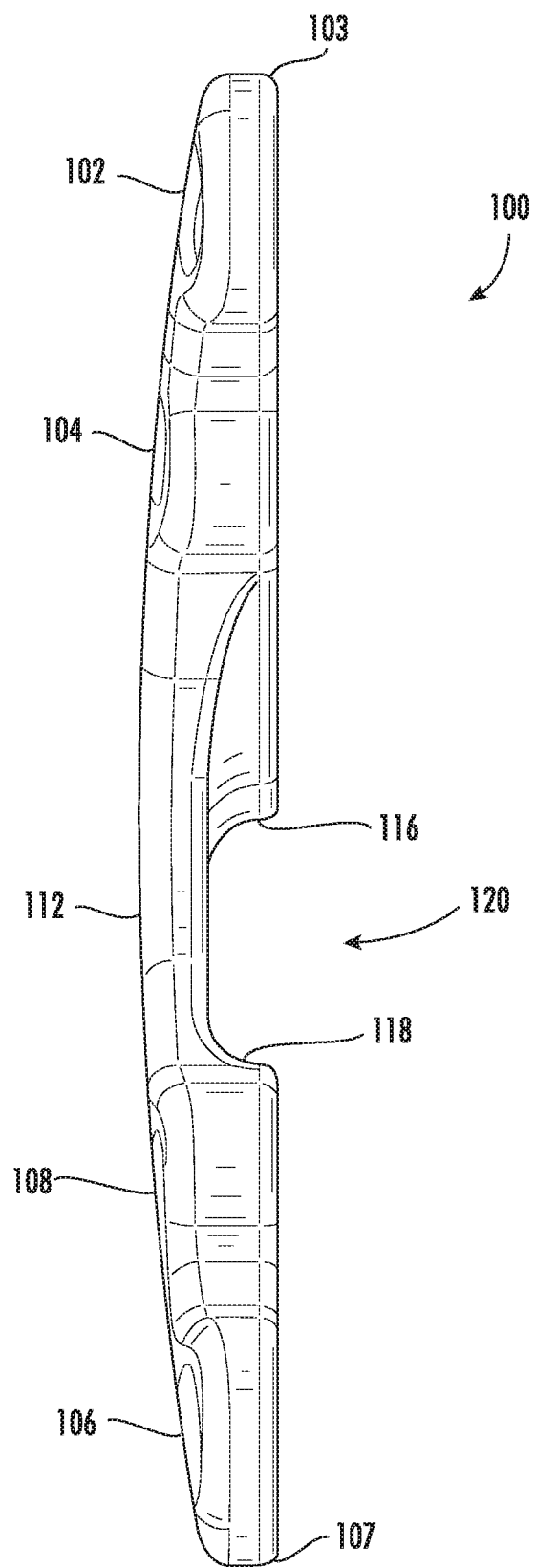
FIG. 4 is a right side elevational view of the neutralization plate.
Figure 5:
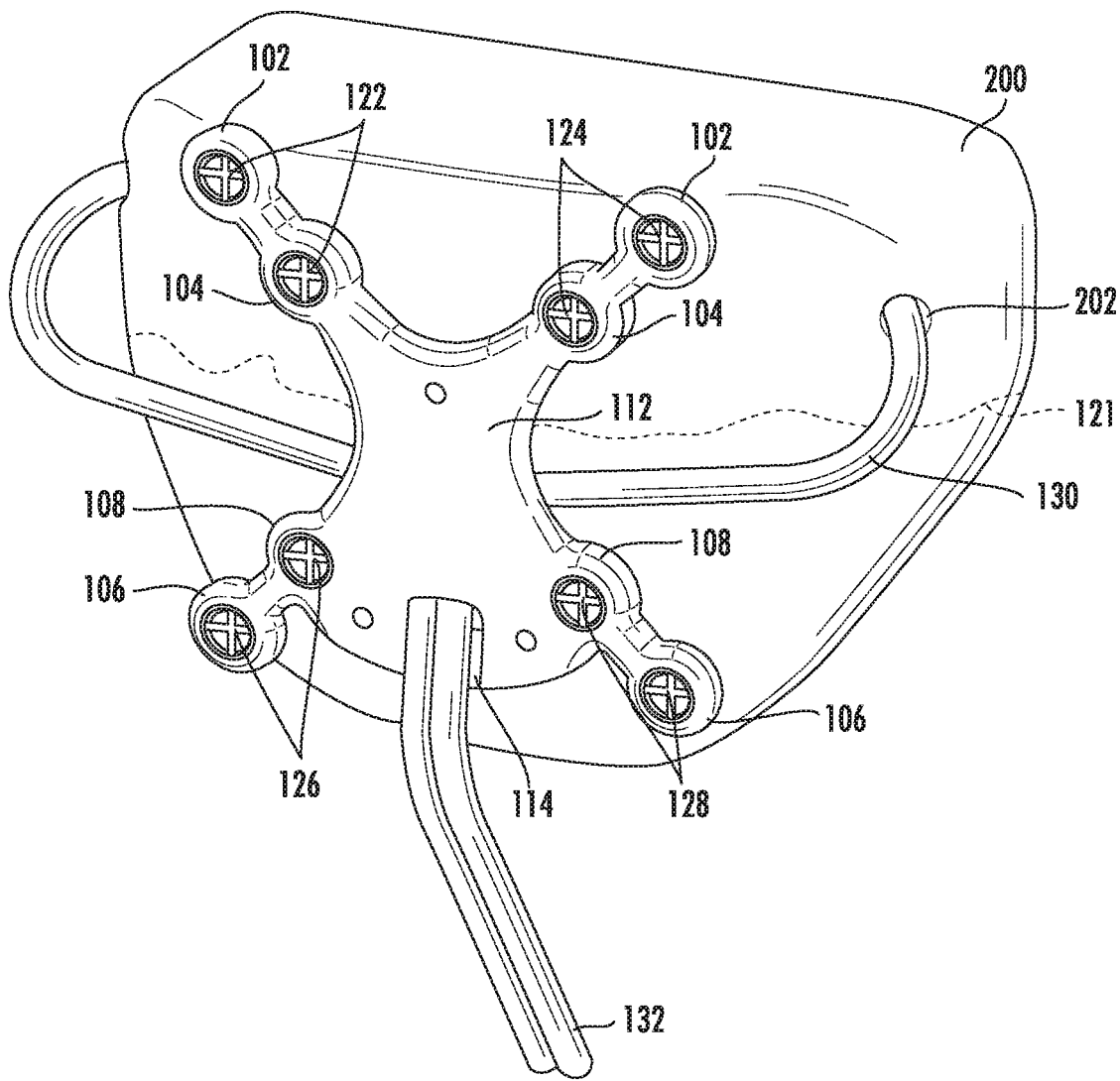
FIG. 5 is a front perspective view of the neutralization plate in place on a patella.
Figure 6:
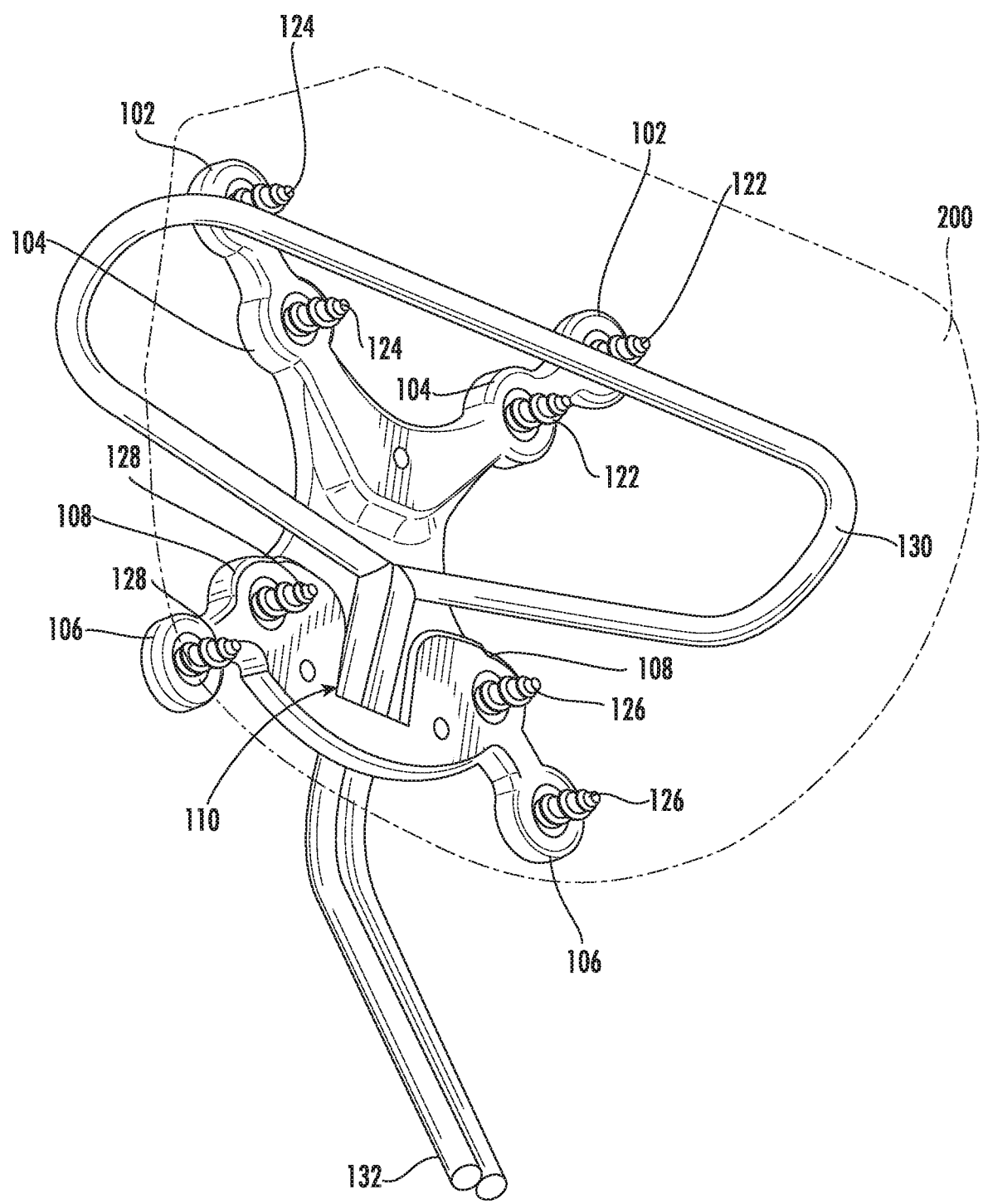
FIG. 6 is a rear perspective view of the neutralization plate on the patella.
Figure 7:
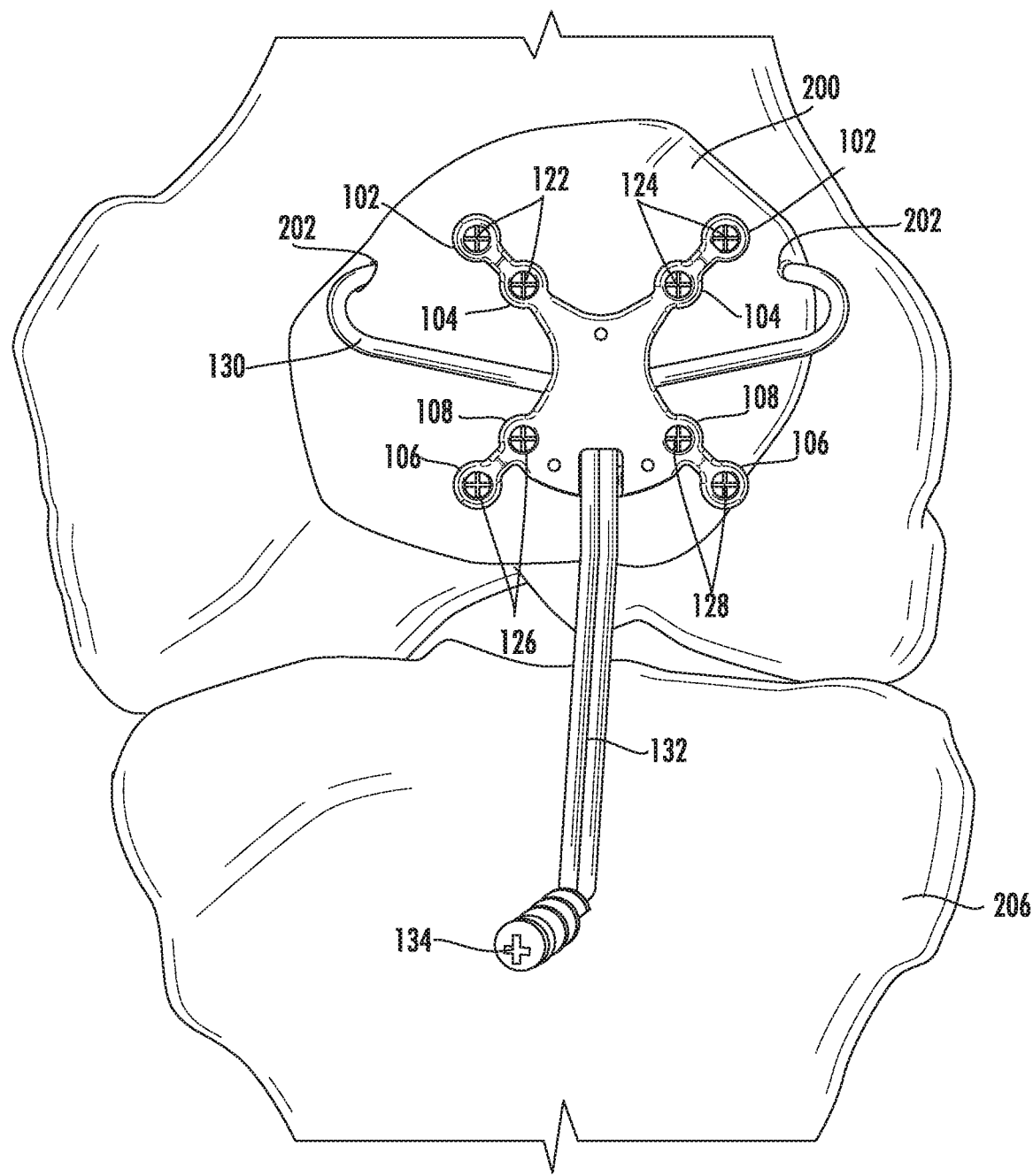
FIG. 7 is a front view of the neutralization plate on the patella.
Figure 8:
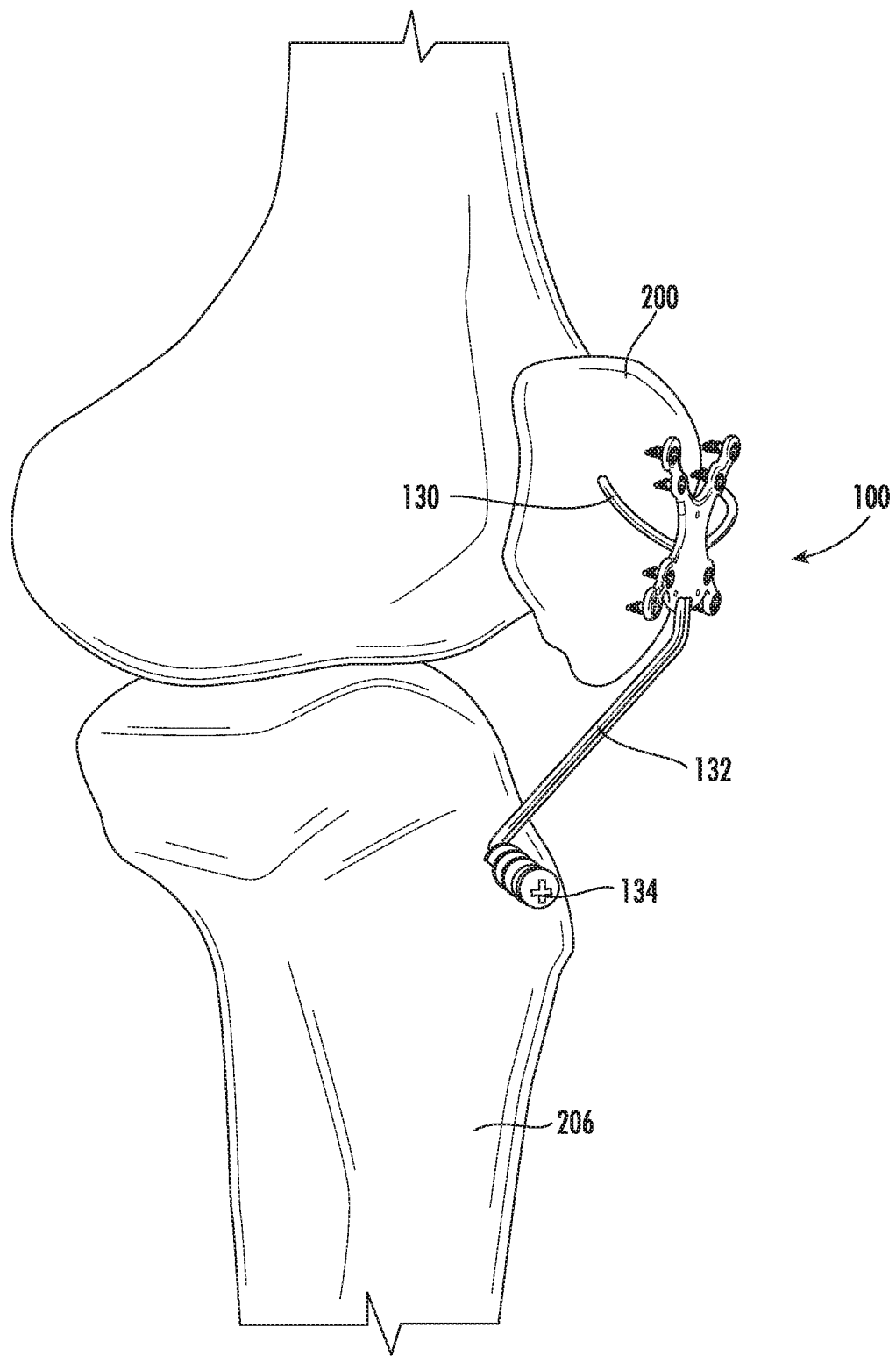
FIG. 8 is a left side perspective view of the neutralization plate on the patella.

Referring now to FIG. 4 showing a side view of the neutralization plate 100, the horizontal channel 120 is formed in the rear side of the neutralization plate 100 between the upper lip 116 and the lower lip 118. The front surface 112 of the main body 112 of the neutralization plate 100 may comprise a smooth texture. The horizontal channel 120 is positioned for the suture 130 to pass between the neutralization plate 100 and the fractured bone 200 where a fracture 121 is located as shown in FIG. 5.

The horizontal channel 120 has a depth that is equal to or greater than a diameter of the suture 130 in order to prevent pinching of the suture 130 between the neutralization plate 100 and the fractured bone 200, so that movement of the suture 130 is not impeded during transition between joint extension and flexion.

As can be seen in FIGS. 5-8, the neutralization plate 100 is mounted to the fractured bone 200 using plating screws 122, 124, 126, 128, which may be locking or non-locking screws. The holes 102, 104, 106, 108 may be threaded, allowing for the optional use of the locking screws at the discretion of the surgeon. The upper arms 103 of the neutralization plate 100 are configured to be secured on one side of a fracture 121 and the lower arms 107 being on an opposing side of the fracture 121.

In addition, the neutralization plate 100 is secured to the fractured bone 200 using the suture and/or wire 130 (described above) that passes through a bore hole 202 formed in the fractured bone 200. The suture 130 enters the bore hole 202 on a first side of the fractured bone 200 and loops through the fractured bone 200 to exit on a second side. The suture 130 is fed through the aperture 110 from a rear side of the neutralization plate 100 down the lower chute 114 as a tail end 132 of the suture 130 extends below the fractured bone 200 and is anchored to a second bone 206 located separate from the fractured bone 200.

In this example, the fractured bone 200 is a patella and the second bone is the tibia 206. This configuration extends fixation and neutralizes the forces tending to pull a fractured patella apart during flexion of the joint (e.g., knee). As can be appreciated by those of ordinary skill in the art, the neutralization plate 100 described herein is not limited to fixation of a tensile fracture of the patella, but is suitable for fixation of many periarticular tensile fractures.

In use, a surgeon begins by reducing the fracture. The surgeon feeds a first end of the suture 130 through the bore hole 202 drilled in the fractured bone 200. The bore hole 202 is generally along a horizontal axis relative to a centerline of the fractured bone 200. Next, the neutralization plate 100 is positioned over the fractured bone 200 so that the upper arms 103 extend above the fracture 121 and the lower arms 107 and aperture 110 are below the fracture 121.

The surgeon feeds the suture 130 through channel 120, down the upper chute 155 and the aperture 110 to the front side of the neutralization plate 100 via the lower chute 114. The surgeon then attaches the neutralization plate 100 to the patella 200 with the plating screws 122, 124, 126, 128. The suture 130 is now ready to be tightened isometrically to the length of the native patella and patellar tendon in knee flexion in this particular example. The suture 130 is then anchored to the tibia 206 using an anchor screw 134. The placement of the suture and/or wire 130 allows for conversion of tensile force during movement into compressive force to hold the fractured bone 200 together.

When properly placed, the neutralization plate 100 functions as a tension band. The configuration of the suture 130 as it passes through the aperture 110 and down the lower chute 114 of the neutralization plate 100 results in advantageously providing fracture compression and neutralization of tensile deforming forces acting across the fixation construct. The low profile of the neutralization plate 100 can be used where current fracture plates are too bulky. The neutralization plate 100 is a vast improvement over the figure eight tension band cable currently being used, which remains prominent, and applies a variable and unknown amount of tension.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A neutralization plate comprising:
    a main body;
    a pair of upper arms extending upwards from the main body;
    a pair of lower arms extending downward from the main body to form a generally X-shape with the pair of upper arms;
    a horizontal channel formed across a rear side of a midsection of the main body;
    an aperture formed in the main body between the pair of lower arms and contiguous to a bottom edge of the horizontal channel; and
    a lower chute formed between the aperture and a lower edge of the horizontal channel;
    wherein the lower chute is configured for ends of a suture looped through a fractured bone to be passed through the aperture and down the lower chute to a front side of the main body to be anchored separately from the fractured bone.

2. The neutralization plate of claim 1, wherein the pair of upper arms comprise an upper hole and an upper secondary hole in each upper arm.

3. The neutralization plate of claim 2, wherein the pair of lower arms comprise a lower hole in each lower arm.

4. The neutralization plate of claim 3, wherein the main body comprises a lower secondary hole spaced inward from each lower hole on the main body.

5. The neutralization plate of claim 1, further comprising an upper chute formed on the rear side of the main body between the aperture and the horizontal channel.

6. The neutralization plate of claim 5, wherein the upper chute and the lower chute are sloped and aligned to each other to increase a transfer of compression forces across a fracture via the suture during joint flexion and to neutralize tension forces.

7. The neutralization plate of claim 5 further comprising an upper lip formed on an upper side of the horizontal channel and a lower lip formed on each side of the upper chute.

8. The neutralization plate of claim 7, wherein the upper lip and the lower lip each comprises an edge thick enough to prevent the suture from slipping up and over a respective lip.

9. The neutralization plate of claim 1, wherein a shape of the neutralization plate is asymmetrical about its horizontal axis.

10. The neutralization plate of claim 1 further comprising screws.

11. The neutralization plate of claim 3, wherein at least one of the upper and lower holes are threaded.

* * * * *